(12) United States Patent
Butler et al.

(10) Patent No.: US 9,603,962 B2
(45) Date of Patent: Mar. 28, 2017

(54) DEVICE FOR EVAPORATING A VOLATILE LIQUID

(75) Inventors: Martin Butler, Hull (GB); Wu Jin, Hull (GB); Chris Jones, Montvale, NJ (US); Kate Langley, Hull (GB); Shaun Rymer, Hull (GB); Steve Walsh, Hull (GB)

(73) Assignee: RECKITT BENCKISER (UK) LIMITED, Slough, Berkshire (GB)

( * ) Notice: Subject to any disclaimer, the term of this patent is extended or adjusted under 35 U.S.C. 154(b) by 2390 days.

(21) Appl. No.: 12/513,703

(22) PCT Filed: Nov. 7, 2007

(86) PCT No.: PCT/GB2007/004252
§ 371 (c)(1),
(2), (4) Date: May 6, 2009

(87) PCT Pub. No.: WO2008/059210
PCT Pub. Date: May 22, 2008

(65) Prior Publication Data
US 2010/0051598 A1    Mar. 4, 2010

(30) Foreign Application Priority Data
Nov. 15, 2006 (GB) .................................. 0622743.3

(51) Int. Cl.
*H05B 1/00* (2006.01)
*A61L 9/03* (2006.01)

(52) U.S. Cl.
CPC .................................. *A61L 9/037* (2013.01)

(58) Field of Classification Search
CPC ... A61L 9/02; A61L 9/03; A61L 9/037; H05K 1/0212; H01L 23/345
(Continued)

(56) References Cited

U.S. PATENT DOCUMENTS 5,412,181 A * 5/1995 Giamati ......................... 219/548
5,684,695 A * 11/1997 Bauer ............................. 701/23
(Continued)

FOREIGN PATENT DOCUMENTS

DE     10305481 A1    8/2004
EP      1196203 A     1/2001
(Continued)

OTHER PUBLICATIONS

English Language Abstract for DE10305481 taken from esp©cenet.com.

*Primary Examiner* — Dana Ross
*Assistant Examiner* — James Sims, III
(74) *Attorney, Agent, or Firm* — Norris McLaughlin & Marcus PA

(57) ABSTRACT

The present invention describes a device for evaporating a volatile liquid from a container having a wick. The device includes a housing, a motion sensor, a first electrical heating element, and at least one of: a second electrical heating element; a fan; a region of increased heating capacity within the first electrical heating element. In use, the motion sensor is operable to detect motion in the vicinity of the device and, on detecting motion, the device operates to activate at least one of a second electrical heating element; a fan; a region of increased heating capacity within the first electrical heating element. The present invention also describes a method for evaporating the volatile liquid and a kit of parts for the same.

19 Claims, 2 Drawing Sheets

(58) Field of Classification Search
USPC .......... 219/209; 222/592, 593, 146.1, 146.2, 222/146.5; 422/1, 5, 120; 392/390, 392, 392/395
See application file for complete search history.

(56) References Cited

U.S. PATENT DOCUMENTS

| | | | |
|---|---|---|---|
| 5,755,381 A * | 5/1998 | Yazaki | .............................. 239/43 |
| 6,104,866 A | 8/2000 | Dewitt | |
| 2004/0033171 A1* | 2/2004 | Kvietok et al. | ............... 422/123 |
| 2004/0247300 A1 | 12/2004 | He | |
| 2005/0139624 A1* | 6/2005 | Hooks et al. | .................. 222/645 |
| 2005/0185392 A1 | 8/2005 | Walter | |
| 2005/0195598 A1* | 9/2005 | Dancs et al. | .................. 362/231 |
| 2005/0201944 A1 | 9/2005 | Kvietok | |

FOREIGN PATENT DOCUMENTS

| | | |
|---|---|---|
| EP | 1522320 A | 4/2005 |
| WO | 2006042873 A | 4/2006 |

\* cited by examiner

DEVICE FOR EVAPORATING A VOLATILE LIQUID

This is an application filed under 35 USC 371 of PCT/GB2007/004252.

The present invention relates to a device for evaporating volatile liquids, for example air fresheners and insecticides. The invention relates in particular to a device for evaporating volatile liquids from a container into a room with the assistance of electrical power.

Devices are known in which a bottle of volatile liquid has a wick projecting therefrom and the device has a heater that is located in the vicinity of the distal end of the wick to accelerate the evaporation of volatile liquid from the wick. The bottle, wick and heater are retained within a casing which carries an electric plug. To operate the heater the device is plugged into a wall socket. Known devices of this type allege to allow control of the rate of evaporation of the volatile liquids, for example, by varying the relative position of the wick and the heater.

A further disadvantage of current devices is the phenomenon of habituation, which occurs especially when one is exposed over a period of time to a constant level of volatile active.

EP 1196203 describes a method of overcoming this phenomenon whereby a constant supply of volatile active is combined with a periodic supply of the same active, thereby "modulating" the total supply in a manner which is constantly changing. This is effected by a manually operated switch on the device.

A further method of overcoming this phenomenon is demonstrated in the device shown in WO 2006/042873, wherein a "boost" of delivery of a volatile active can be selected by manually pressing a button, said boost being delivered either by a fan or by a further heater, or by both.

All of the above mentioned prior art suffer from the drawback of efficiency and convenience, in that the user has to manually change the apparatus from "normal" to "boost" or "modulate" mode, and then to switch it back to normal mode when this effect is no longer necessary (e.g. when the room is empty, or at night). Given the typical location of sources of electrical supply on walls (at a low level near the floor), this makes the process more inefficient and inconvenient.

There is a need therefore for a device which overcomes the defects of the prior art and provides a timely and efficient alteration of the fragrance supply to a room, thereby overcoming the effects of habituation, whilst at the same time minimising excess delivery of volatile active. According to a first aspect of the present invention there is provided therefore a device for evaporating a volatile liquid from a container having a wick with a proximal end region within the container and a distal end region above the container, the device comprising:
a housing;
securing means within said housing to releasably secure the container to the device;
a first electrical heating means;
motion sensor means;
and wherein the motion sensor means is operable, in use, to detect motion in the vicinity of the device and, on detecting motion, is further operable to cause the activation of at least one of: a second electrical heating means; a fan; a region of increased heating capacity within the first electrical heating means.

Preferably when, in use, the motion sensor means detects motion in the vicinity of the device the sensor means is operable to cause the activation of at least two of: a second electrical heating means; a fan; a region of increased heating capacity within the first electrical heating means.

Even more preferably when, in use, the motion sensor means detects motion in the vicinity of the device the sensor means is operable to cause the activation of a second electrical heating means, and a fan, and a region of increased heating capacity within the first electrical heating means.

In one embodiment the first electrical heating means may be operable, in use, and in the absence of motion being detected, to activate on a routine cycle where said first heating means is activated for a period of time ($t_1$) followed by a rest period of non-activation (x). $t_1$ may have an range of 0.1-120 minutes and x have a range of 0.1-120 minutes. Preferably $t_1$ has a range of 5-90 minutes and x has a range of 5-60 minutes. Most preferably $t_1$ has a range of 20-60 minutes and x has a range of 10-30 minutes.

When motion is detected, in use, the at least one of: a second electrical heating means; a fan; and/or a region of increased heating capacity within the first heating means may be operable to activate for a period of time ($t_2$) followed by a rest period of non-activation (y).

$t_2$ may have an range of 1-120 minutes and y have a range of 1-60 minutes. Preferably $t_2$ has a range of 10-90 minutes and y has a range of 5-30 minutes. Most preferably $t_2$ has a range of 20-60 minutes and y has a range of 10-20 minutes.

Preferably $t_2 \leq t_1$ and $y \leq x$. Even more preferably $t_2 = t_1/2$ and $y = x$.

Alternatively or additionally, in use, and in the absence of motion being detected, the first electrical heating means may be operable to activate on a routine cycle where said first heating means is activated for a period of time $t_4$ at full power (so-called 100% duty cycle), followed by a period of activation at lower power for time $t_5$ (50-99% duty cycle, and preferably 60-80%) before being followed by a rest period for time x (substantially 0% duty cycle). $t_4$ may have a range of 0.05-119.95 minutes and $t_5$=0.05-119.95 minutes. Preferably $t_4$ has a range of 0.05-89.95 minutes and $t_5$ has a range of 0.05-89.95 minutes. Most preferably $t_4$ has a range of 0.05-59.95 minutes and $t_5$ has a range of 0.05-59.95 minutes In an alternative embodiment the first electrical heating means may be operable, in use, and in the absence of motion being detected, to be activated constantly.

When motion is detected, in use, the at least one of: a second electrical heating means; a fan; and/or a region of increased heating capacity within the first heating means may be operable to activate for a period of time ($t_2$) followed by a rest period of non-activation (y). $t_2$ may have a range of 1-120 minutes and y have a range of 1-60 minutes. Preferably $t_2$ has a range of 10-90 minutes and y has a range of 5-30 minutes. Most preferably $t_2$ has a range of 20-60 minutes and y has a range of 10-20 minutes.

Alternatively or additionally, in use, and in the absence of motion being detected, the first electrical heating means may be operable to activate on a routine cycle where said first heating means is activated for a period of time $t_4$ at full power (so-called 100% duty cycle), followed by a period of activation at lower power for time $t_5$ (50-99% duty cycle, and preferably 60-80%). $t_4$ may have a range of 1-120 minutes and $t_5$=1-120 minutes. Preferably $t_4$ has a range of 1-90 minutes and $t_5$ has a range of 1-90 minutes. Most preferably $t_4$ has a range of 1-60 minutes and $t_5$ has a range of 1-60 minutes For either of the above-mentioned embodiments, the first and/or second heating means and/or fan may be located within the device in a position suitable to direct heat and/or a current of air, respectively, toward the area where the distil end of the wick would be located when a container is releasably secured to the housing.

Preferably the first and/or second heating means and/or fan may be located within the device in a position substantially adjacent to the area where the distil end of the wick would be located when a container is releasably secured to the housing.

The device of the present invention may be advantageous because the device is adapted to be responsive to the conditions of the environment surrounding it. In particular, when the device senses motion in the surrounding vicinity it is operable to increase the rate of volatilisation thus, in use, increasing the quantity of volatilised liquid in the environment surrounding the device. This increase in volatilisation may be capable of minimising or overcoming the habituation phenomenon.

When present, rest periods x and y may advantageously provide the device with a degree of self regulation to prevent the device, in use, from causing volatilisation every time motion is detected. This may also prevent the environment surrounding the device from becoming saturated with volatilised liquid.

The motion sensor means may be provided in the form of at least one of: an infrared (IR) sensor; a laser sensor; and a sound sensor.

The IR sensor, which is preferably a passive IR sensor, may be operable to detect radiation in the infrared spectrum, thus be capable of detecting the presence of a person or an animal within the vicinity of the device. The laser sensor may be operable to emit one or more laser beams and be adapted to detect when an object breaks the one or more beams by moving across the beam(s), thus indicating the presence of a person or an animal within the vicinity of the device. The sound sensor may be operable to detect sound within the vicinity of the device and, preferably, once the detected sound exceeds a predefined level this is indicative of movement within the vicinity of the device.

Preferably the motion sensor means is provided in the form of at least two of: an infrared (IR) sensor; a laser sensor; and a sound sensor. Most preferably the motion sensor means is provided in the form of an infrared (IR) sensor and a laser sensor and a sound sensor.

Motion within the vicinity of a device according to the present invention may be defined as one or more 'motion events' within the vicinity of the device. The motion sensor means may be operable to detect each motion event within the vicinity of the device and communicate each event to the controller and/or directly to the first and/or second heating means and/or fan. Alternatively or additionally, the motion sensor means may only communicate the detection of a motion event to the controller once a predefined number of motion events have been detected. As a further alternative or additional arrangement, the controller may only communicate with the first and/or second heating means and/or fan once a predefined number of motion events have been communicated to the controller by the motion sensor means.

The number of predefined motion events that may be required in order to cause the activation of the first and/or second heating means and/or fan may be fixed or may be selectable by a user. The possibility for a user to select the number of predetermined motion events required to trigger the activation may be advantageous as a user can modify the number based on the location of the device and the user's requirements of the device.

The first and/or second heating means may be provided in any suitable form such as a bar heater or at least one point source resistor. Preferably said heating means is/are provided in the form of at least one electrical resistor, such as a thermistor.

The first and/or second heating means may be able to provide, in use, heat to the distal end of a wick in the range of 50-120° C., preferably heat in the range of 50-100° C., and most preferably heat in the range of 55-90° C.

Alternatively of additionally, the first and/or second heating means may be able to provide, in use, heat to the distal end of a wick in the range of 40-95% of the flash point of the volatile liquid, preferably heat in the range of 50-90%, and most preferably heat in the range of 55-75%.

Preferably there is a controller operably connected to the motion sensor means. The controller may also be operably connected to the first and/or second heating means and/or fan to control the operation thereof relative to each other.

The electrical power applied to the device may by provided by any suitable form, such as by mains electricity, batteries or solar cells. However, due to the power demands of the heating means, mains electricity is preferred.

Where the device is intended for use with mains electricity, the device may be provided with plug formations configured to engage the openings in a mains electrical socket. Alternatively, a device for use with mains electricity may be provided with a cable having plug formations located at a distal end thereof to permit the device to be located remotely from a mains electrical socket.

Where the device is provided with the plug formations, the formations are located toward a generally rear-facing aspect of the housing and, in this arrangement, the securing means can be located in a lower-facing aspect of the housing and the upper aperture of the chimney means can be located in an upper aspect of the housing.

The housing may be providing with one or more exit chimney means to facilitate the emanation of the volatilised liquid from the device. Additionally, the housing may have one or more vents suitable to allow the fan to draw a current of air through the device toward the location of the distal end of the wick of a container when said container is releasably engaged with the device.

The housing is preferably substantially open toward the lower aspect thereof to permit convenient access to, and sight of, a container when releasably held by the securing means. This arrangement may be advantageous since a user will be able to visually monitor the level of volatile liquid remaining in the container.

Alternatively, the housing may substantially surround the container when the container is held by the securing means. This arrangement may be advantageous as an engaged container may be less susceptible to being tampered with. Additionally, this arrangement may permit the device to have an improved aesthetic from a consumer perspective.

The securing means may engage any part of the container to ensure the position of the container in relation to the device. Preferably the securing means are arranged to engage with an upper portion of the container since this arrangement may facilitate a more reliable positioning of the wick within the device.

Alternatively, the securing means may engage a lower portion of the container. This arrangement may be particularly useful where the housing is arranged to substantially surround an engaged container.

The securing means may be arranged to engage more than one portion of the container.

The volatile liquid may be provided in the form of an air freshener, a deodorant, a perfume, an odourant, an insecticide, a fungicide and/or variants thereof.

The device may be operable in a normal mode or a detection mode; wherein in normal mode the first electrical heating means may be operable, in use, to activate continually or at the time interval of $t_1$ (depending on the embodiment) and wherein in detection mode the motion sensor means may be operable, in use, to detect motion in the vicinity of the device and communicate any detection to the controller and/or the first and/or second electrical heating means and/or fan to cause the activation thereof at the time interval of $t_2$.

The device may be switchable between the normal mode and the detection mode. The device may be manually and/or automatically switchable between the normal mode and the detection mode. Automatic switching between normal mode and detection mode may be controlled by a timing mechanism and/or a sensor operably connected to the controller, such as a light sensor and/or sound detection means.

The incorporation of a timing mechanism to effect the switching of the device between a normal mode and a detection mode may be advantageous as a user can select when the detection mode may be operable, thus, providing a user with a greater level of control of the rate of volatilisation in response to motion being detected. This level of control will also permit a user to conserve the power consumption of the device by controlling the amount of time the device is in the detection mode, thus, controlling when the motion sensor means may consume power.

Furthermore, the incorporation of a sensor to effect the switching of the device between a normal mode and a detection mode may be advantageous as a user can allow the device to automatically cause the switching between a normal mode and a detection mode providing a user with a greater level of control in response to motion being detected. For instance, a light sensor may be used to only allow the switching when light is detected such that motion at night does not cause additional activation. Whereas a sound detection means may permit the switching into the detection mode only when sound is detected, thus, preventing the motion sensor means from consuming power until sound is detected, the sound possibly being indicative of the environment around the device being used.

The device may be provided with an indicator wherein said indicator is operable to indicate to a user what function the device is currently performing. The indicator may be operable to provide a visual indication and/or provide an audible indication.

Preferably the indicator is configured to provide a visual indication by emitting light from one or more light sources, preferably one or more LEDs.

The one or more light sources may be adapted to emit a different colour of light to indicate the current function the device is performing. Additionally or alternatively, the one or more light sources may blink or flash to indicate the current function the device is performing.

Alternatively or additionally, the device may be operable to visually indicate the function currently being performed by the device via a screen. The screen may be an LCD screen that is adapted to provide a message to a user, for instance such messages could include "ON", "SENSING", "MOTION DETECTED", "RESTING", "NORMAL MODE", "DETECTION MODE", "OFF".

The device may be provided with a boost mechanism. The boost mechanism may be linked to a user operated switch or button or the like. On operating the boost mechanism the activation of at least one of: a second electrical heating means; a fan; a region of increased heating capacity within the first electrical heating means may occur regardless of the current mode of operation of the device. In effect, the boost mechanism may provide the user with a control to override the operation of the device to initiate a specific activation.

According to a second aspect of the present invention there is provided therefore a method of evaporating a volatile liquid from a container of volatile liquid, the method comprising the steps of:

loading a container of volatile liquid into a device according to the first aspect of the present invention;

placing the device in an operational mode wherein the motion sensor means is capable of detecting motion in the vicinity of the device;

and wherein, upon detection of motion by said motion sensor means, said motion causes the activation of at least one of: a second electrical heating means; a fan; a region of increased heating capacity within the first electrical heating means.

According to a third aspect of the present invention there is provided therefore a kit of parts for evaporating a quantity of volatile liquid, said kit comprising a device in accordance with the first aspect of the present invention, said device being adapted to operate in accordance with the method according to the second aspect of the present invention, and further comprising a container of fluid wherein said container is configured to be loadable into the housing of the device.

Embodiments of the invention will now be described, by way of example only, with reference to the accompanying drawings in which.

Figure 1:
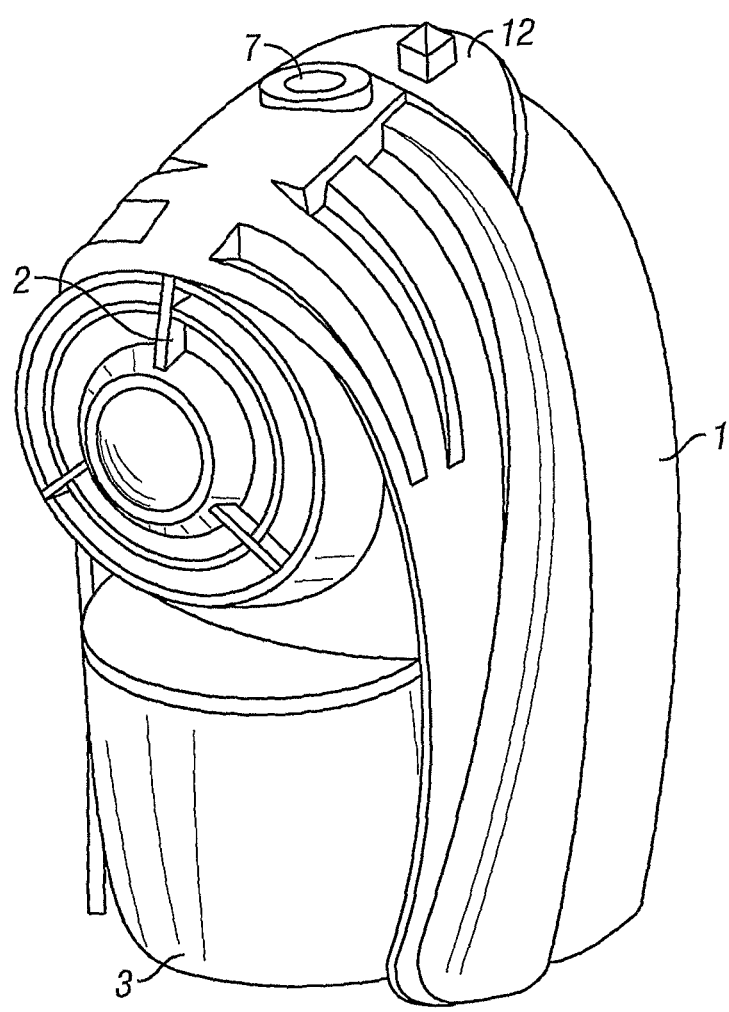
FIG. 1 illustrates a perspective view of a device of the present invention.
Figure 2:
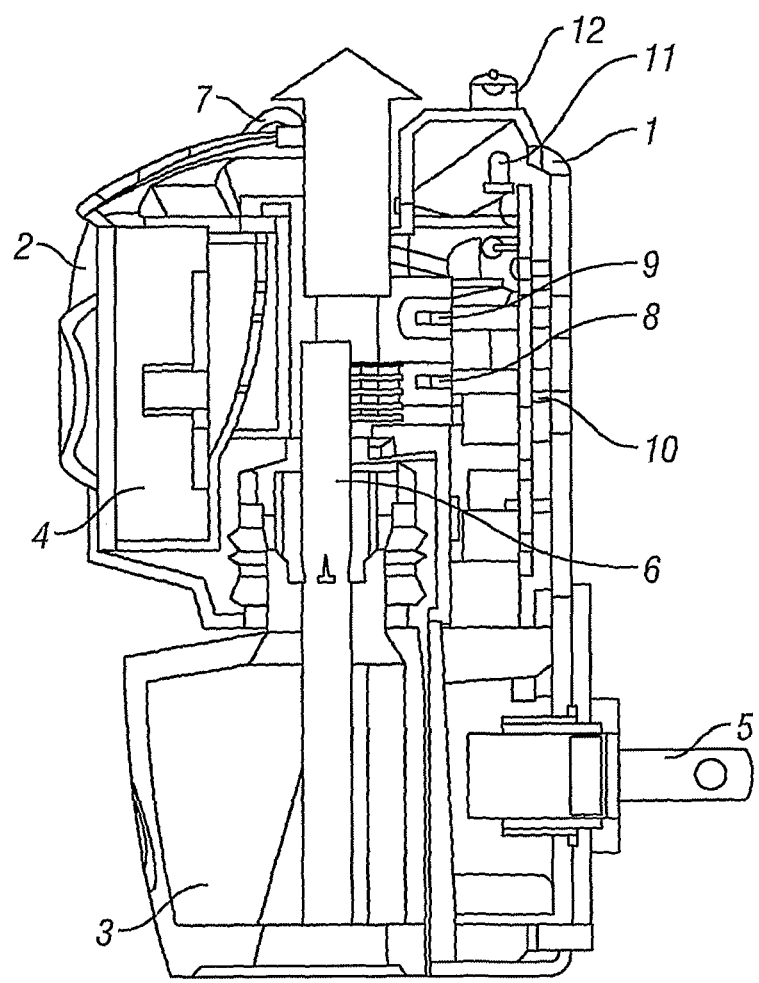
FIG. 2 illustrates a sectioned side view of a device of the present invention.

In general terms, the device 1 illustrated in FIGS. 1 & 2 is shown with a container of volatile liquid engaged therewith. The container has a reservoir portion in the form of a glass bottle containing a volatile liquid 3 and a wick 6 extending into the bottle. The wick 6 also extends above the top of the bottle through a seal and into a chimney means of the device 1. The wick 6 may be substantially cylindrical. The seal is present to retain the liquid 3 within the bottle should the device 1 be knocked over and/or inverted when the container is engaged therewith.

The device 1 has a housing 2 which partially extends over the container and its upper part. From the rear wall of the housing extends electrical plug formations 5.

The top of the housing 2 has a generally circular central aperture which defines the upper aperture of the chimney means. The upper aperture is aligned with a co-axial lower aperture (not shown), thus defining a channel therebetween for volatilised liquid to flow up and out of the upper aperture into the environment surrounding the device 1.

A first electrical heating means 8 and second electrical heating means 9, if present, may be provided in the form of separate resistors, and preferably as positive temperature coefficient (PTC) thermistors. However, either of both of the first or second electrical heating means 8,9 could be provided by way of a ring heater or the like, or a combination thereof.

An electrical fan 4 may also be provided. All of the fan 4 and the first and second electrical heating means 8,9 are in operable communication, either directly or indirectly, with a motion sensor means 12, illustrated as a PIR motion sensor in FIGS. 1 and 2.

Indirect operable communication may be via a controller (not shown) which could act as the principal receiver of information from the motion sensor 12, process the provided information and direct the control of the aforementioned components.

An example of one mode of operation of the device and the inter-relation of the components will now be explained.

The device 1 must first be placed in an operational mode. There may be a user-activated switch (not shown) to permit the device to be switched into the operational mode. The device 1 will draw power from the power source which is depicted as plug formations 4 to draw mains electrical power, this could be from solar cells mounted on the device and/or one or more batteries however.

Initiating the operational mode will cause the first heater means 8 to warm up to a temperature that will cause the evaporation of the volatile liquid from the device 1. In the absence of the detection mode and/or motion being detected, the first heater means 8 will continue to impart heat toward the wick for a period of time $t_1$ and, at the end of $t_1$ the heater means 8 will go into a rest period for time x where the heater means 8 will not draw any power.

A user controlled switch (not shown) may be provided to allow a user to adjust the value of $t_1$ and/or x.

However, the motion sensor means 12 may also draw power, either constantly or periodically, in order to sense for movement in the vicinity of the device 1. If the motion sensor means 12 senses movement it is operable to communicate this information to the controller (not shown). Once the controller has received this information it is operable to instruct the activation of at least one of: the second heater means 9; the fan 4; and/or a range of higher temperature in the first heater means 8; thus causing an increase in the rate of evaporation of the volatile liquid for a time interval of $t_2$. At the end of time interval $t_2$ the at least one of: the second heater means 9; the fan 4; and/or a range of higher temperature in the first heater means 8 will go into a rest period for time interval y where said means' and/or fan will not draw any power.

Subsequent detection of motion by the motion sensor means 12 may also be communicated to the controller which will cause the activation of the at least one of: the second heater means 9; the fan 4; and/or a range of higher temperature in the first heater means 8 means only if time period y has elapsed.

When the device is first placed in an operational mode the controller may cause the activation to occur substantially immediately or after a short delay, say after 2 minutes.

Alternatively the controller may, after the first heater means 8 has been activated following being placed in an operational mode and on being informed of detection of motion within the vicinity of the device, delay causing the activation of the at least one of: the second heater means 9; the fan 4; and/or a range of higher temperature in the first heater means 8, until a predetermined interval of time $t_3$ has elapsed. Once time period $t_3$ has elapsed subsequent activation following the detection of motion would take place at a time interval of $t_2$.

Alternatively, when the operational mode is initiated the first heater means 8 will warm up to a temperature that will cause evaporation of the volatile liquid and this heater means will remain activated without rest period x.

The device may be manually or automatically switchable between a normal mode and a detection mode. Such automatic switching may be controlled by a timing mechanism and/or a sensor operably connected to the controller, such as a light sensor and/or sound detection means. The automatic switching may permit the device to consume less power by only permitting the device to operate in the detection mode of a limited period of time, thus conserving the power consumed by the motion sensor means 12. Such conservation of power being particularly useful where the device is powered by batteries and/or solar cell(s).

The motion sensor means 12 may have a lens cover which protrudes from the front of the device 1 to ensure a wide field of view. This may be advantageous where the motion sensor means is a passive infra-red sensor, since the motion would not need to be directly in front of the sensor means to be detected. Similarly, where the motion sensor means 12 is additionally or alternatively provided as a laser sensor this will also afford such sensors a wide field of view.

The illustrated device 1 is shown having an indicator 11 which is provided in the form of an LED. The LED(s) may be operable to provide a visual indication of the function currently being performed by the device. For instance, the LED could indicate when the device is in an operational mode by emitting a constant light which is converted to a flashing operation when motion has been detected.

The indicator 11 may also be provided with an audio component (not shown) wherein this component is capable of giving an audible alert when a particular function is being performed and/or motion has been detected or the like.

Alternatively or additionally, a screen (such as an LCD screen) could be presented on a prominent part of the device 1 to provide a message to a user indicating the current functioning of the device 1. For instance such messages could include "ON", "SENSING", "MOTION DETECTED", "RESTING", "NORMAL MODE", "DETECTION MODE", "OFF".

The above description describes an embodiment comprising a controller, however, where the controller is not present the components may be inter-connected to be operably communicative with each other to implement the above-mentioned operational relationship.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method of evaporating a volatile liquid from a container of volatile liquid, the method comprising the steps of:
   loading a container of volatile liquid into a device which comprises:
   a housing;
   securing means within said housing to releasably secure the container to the device;
   a first electrical heating means;

motion sensor means, wherein the motion sensor means is at least one of: an infrared (IR) sensor; a laser sensor; a sound sensor; and at least one of: a second electrical heating means; a fan; a range of higher temperature in the first electrical heating means;

placing the device in an operational mode wherein the motion sensor means is capable of detecting motion in the vicinity of the device;

and wherein, upon detection of motion by said motion sensor means, said motion causes the activation of at least one of: the second electrical heating means; the fan; the range of higher temperature in the first electrical heating means.

2. The method according to claim 1, wherein upon detection of motion by said motion sensor means, said motion causes the activation of at least two of: the second electrical heating means; the fan; the range of higher temperature in the first electrical heating means.

3. The method according to claim 2, wherein upon detection of motion by said motion sensor means, said motion causes the activation of each of: the second electrical heating means; the fan; and the range of higher temperature in the first electrical heating means.

4. The method according to claim 1, wherein in the absence of motion being detected the first electrical heating means is activated on a routine cycle where said first heating means is activated for a period of time $t_1$ followed by a rest period of non-activation x, where $t_1$ has a range of 0.1-120 minutes and x has a range of 0.1-120 minutes.

5. The method according to claim 4, wherein $t_1$ has a range of 5-90 minutes and x has a range of 5-60 minutes.

6. The method according to claim 1, wherein in the absence of motion being detected, the first electrical heating means is activated on a routine cycle where said first heating means is activated for a period of time $t_4$ at full power followed by a period of activation at a lower power for time $t_5$, followed by a rest period of non-activation for time x, wherein $t_4$ has a range of 0.005-119.95 minutes and $t_5$ has a range of 0.05-119.95 minutes.

7. The method according to claim 6, wherein $t_4$ has a range of 0.05-89.95 minutes and $t_5$ has a range of 0.05-89.95 minutes.

8. A method according to claim 1, wherein in the absence of motion being detected the first electrical heating means is activated on a routine cycle where said first heating means is activated for a period of time $t_1$ followed by a rest period of non-activation x, where $t_1$ has a range of 0.1-120 minutes and x has a range of 0.1-120 minutes;

wherein when motion is detected, the at least one of: the second electrical heating means; the fan; the range of higher temperature in the first electrical heating means is activated for a period of time $t_2$ followed by a rest period of non-activation y, where $t_2$ has a range of 1-120 minutes and y has a range of 5-30 minutes, and wherein $t_2 \leq t_1$ and $y \leq x$.

9. A method according to claim 8, wherein $t_2 = t_1/2$ and $y = x$.

10. The method according to claim 1, wherein the container comprises: a wick having a proximal end region within the container and a distal end region above the container.

11. The method according to claim 1, wherein when motion is detected, the at least one of: the second electrical heating means; the fan; the range of higher temperature in the first electrical heating means is activated for a period of time $t_2$ followed by a rest period of non-activation y, where $t_2$ has a range of 1-120 minutes and y has a range of 5-30 minutes.

12. A method according to claim 1, wherein the first electrical heating means is operable to be activated constantly.

13. A method according to claim 1, wherein first electrical heating means is operable to activate on a routine cycle where said first heating means is activated for a period of time $t_4$ at full power, followed by a period of activation at a lower power for time $t_5$, wherein $t_4$ has a range of 1-120 minutes and $t_5$ has a range of 1-120 minutes, and preferably $t_4$ has a range of 1-90 minutes and $t_5$ has a range of 1-90 minutes.

14. A method according to claim 1, wherein the motion sensor means only communicates the detection of a motion event once a predefined number of motion events have been detected.

15. A method according to claim 1, wherein the user of the device may select a number of predefined motion events that are required in order to cause the activation of the first and/or second heating means and/or fan.

16. A kit of parts for evaporating a quantity of volatile liquid, said kit comprising a device which comprises:

a housing;

securing means within said housing to releasably secure a container to the device;

a first electrical heating means;

motion sensor means, wherein the motion sensor means is at least one of: an infrared (IR) sensor; a laser sensor; a sound sensor;

and at least one of: a second electrical heating means; a fan; a range of higher temperature in the first electrical heating means;

and further comprising a container of volatile fluid wherein said container is configured to be loadable into the housing of the device, said device adapted to operate according to a method comprising the steps of:

loading the container of volatile liquid into the device;

placing the device in an operational mode wherein the motion sensor means is capable of detecting motion in the vicinity of the device;

and wherein, upon detection of motion by said motion sensor means, said motion causes the activation of at least one of: the second electrical heating means; the fan; the range of higher temperature in the first electrical heating means.

17. The kit according to claim 16, wherein upon detection of motion by said motion sensor means, said motion causes the activation of at least two of: the second electrical heating means; the fan; the range of higher temperature in the first electrical heating means.

18. The kit according to claim 17, wherein upon detection of motion by said motion sensor means, said motion causes the activation of each of: the second electrical heating means; the fan; and the range of higher temperature in the first electrical heating means.

19. The kit according to claim 16, wherein the container comprises: a wick having a proximal end region within the container and a distal end region above the container.

* * * * *